(12) United States Patent
Khare

(10) Patent No.: US 8,461,404 B2
(45) Date of Patent: Jun. 11, 2013

(54) AROMATIZATION CATALYST COMPRISING PROLONGATED SILICA AND METHODS OF MAKING AND USING SAME

(75) Inventor: Gyanesh P. Khare, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 13/028,812

(22) Filed: Feb. 16, 2011

(65) Prior Publication Data

US 2011/0137092 A1   Jun. 9, 2011

Related U.S. Application Data

(62) Division of application No. 11/870,972, filed on Oct. 11, 2007, now Pat. No. 7,902,105.

(51) Int. Cl.
  *C07C 5/10* (2006.01)
  *C07C 5/00* (2006.01)
  *C07C 2/00* (2006.01)

(52) U.S. Cl.
  USPC ........... 585/254; 585/319; 585/322; 585/323; 585/407; 585/410; 585/411; 585/418; 585/419

(58) Field of Classification Search
  USPC ................. 585/254, 319, 322, 323, 407, 410, 585/411, 418, 419
  See application file for complete search history.

(56) References Cited

U.S. PATENT DOCUMENTS

| | | | |
|---|---|---|---|
| 3,216,789 A | 11/1965 | Breck et al. | |
| 4,830,732 A | 5/1989 | Mohr et al. | |
| 5,106,803 A | 4/1992 | Mohr et al. | |
| 5,294,579 A | 3/1994 | Ohashi et al. | |
| 5,354,933 A * | 10/1994 | Ohashi et al. | 585/419 |
| 5,366,617 A | 11/1994 | Bradley et al. | |
| 5,514,362 A | 5/1996 | Miller | |
| 5,558,851 A | 9/1996 | Miller | |
| 5,919,722 A | 7/1999 | Verduijn et al. | |
| 6,096,936 A | 8/2000 | Fukunaga et al. | |
| 6,107,236 A | 8/2000 | Pecoraro et al. | |
| 6,132,595 A | 10/2000 | Bogdan et al. | |
| 6,207,042 B1 | 3/2001 | Holtermann et al. | |
| 6,372,685 B1 | 4/2002 | Pecoraro et al. | |
| 7,902,105 B2 | 3/2011 | Khare | |
| 2002/0193240 A1 | 12/2002 | Fukunaga | |
| 2004/0259719 A1* | 12/2004 | Wu | 502/66 |

FOREIGN PATENT DOCUMENTS

| | | |
|---|---|---|
| JP | 2004009029 A | 1/2004 |
| WO | 9106367 A2 | 5/1991 |
| WO | 03033146 A1 | 4/2003 |
| WO | 2009048755 A2 | 4/2009 |
| WO | 2009048755 A3 | 4/2009 |

OTHER PUBLICATIONS

Foreign communication from a counterpart application—International Preliminary Report on Patentability, PCT/US2008/077937, Apr. 22, 2010, 8 pages.
Foreign communication from a counterpart application—International Search Report and Written Opinion, PCT/US2008/077937, Oct. 2, 2009, 17 pages.
Foreign communication from a related counterpart application—Invitation to Pay Additional Fees, PCT/US2008/077937, May 28, 2009, 6 pages.
Machine translation of JP 2004009029, May 12, 2009, 8 pages, TXTJPT.
Fukunaga, Tetsaya, et al., "Halogen-promoted Pt/KL Zeolite Catalyst for the Production of Aromatic Hydrocarbons from Light Naphtha," Catal. Surv. Asia, vol. 14, pp. 96-102, Jun. 4, 2010, Springer.

* cited by examiner

*Primary Examiner* — Elizabeth Wood
(74) *Attorney, Agent, or Firm* — Conley Rose, P.C.; Rodney B. Carroll; Chad E. Walter

(57) ABSTRACT

A prolongated silica bound zeolite support comprising from about 85 wt % to about 95 wt % zeolite. A catalyst composition comprising a prolongated silica bound zeolite supporting at least one Group VIII metal and at least one halide. A process of making a prolongated silica bound zeolite support comprising mixing a zeolite, a prolongated silica, and water to form a mixture, and shaping the mixture into the prolongated silica bound zeolite support. A process of making a prolongated silica bound zeolite catalyst comprising mixing a zeolite, a prolongated silica, and water to form a mixture, shaping the mixture into a prolongated silica bound zeolite support, and adding one or more catalytic compounds to the prolongated silica bound zeolite support to form the prolongated silica bound zeolite catalyst. A process for converting hydrocarbons to aromatics comprising: contacting a prolongated silica bound zeolite catalyst comprising at least one Group VIII metal and at least one halide with a hydrocarbon feed in a reaction zone under aromatization conditions; recovering an aromatic product from the reaction zone; and purifying the aromatic product to produce benzene, toluene, paraxylene, orthoxylene, metaxylene, or combinations thereof.

23 Claims, 1 Drawing Sheet

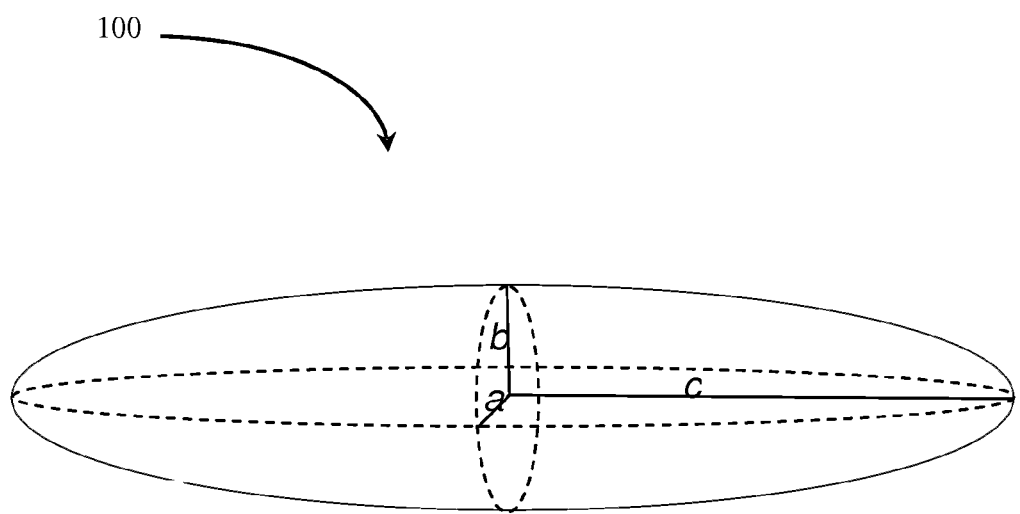

AROMATIZATION CATALYST COMPRISING PROLONGATED SILICA AND METHODS OF MAKING AND USING SAME

CROSS-REFERENCE TO RELATED APPLICATIONS

This is a Divisional Application of U.S. patent application Ser. No. 11/870,972 filed Oct. 11, 2007, now U.S. Pat. No. 7,902,105, and entitled "Aromatization Catalyst Comprising Prolongated Silica And Methods Of Making And Using Same," which application is hereby incorporated by reference herein in its entirety.

FIELD OF THE INVENTION

The present disclosure relates to catalyst compositions. More specifically, the present disclosure relates to improved aromatization catalyst compositions and methods of producing same.

BACKGROUND OF THE INVENTION

Large pore zeolite catalysts are useful to dehydrocyclize aliphatic hydrocarbons to produce aromatic hydrocarbons. For example, large pore zeolite catalysts are useful for reforming light petroleum naphtha (e.g. $C_6$-$C_8$) to benzene, toluene and xylenes. Examples of such aromatization catalysts include silica bound large pore zeolite supports containing platinum and halides such as chloride and fluoride. Due to the commercial importance of such catalysts, an ongoing need exists for improved aromatization catalysts and methods of making and using same.

SUMMARY OF THE INVENTION

Disclosed herein is a prolongated silica bound zeolite support comprising from about 50 wt % to about 95 wt % zeolite.

Also disclosed herein is a catalyst composition comprising a prolongated silica bound zeolite supporting at least one Group VIII metal and at least one halide.

Further disclosed herein is a process of making a prolongated silica bound zeolite support comprising mixing a zeolite, a prolongated silica, and water to form a mixture, and shaping the mixture into the prolongated silica bound zeolite support.

Further disclosed herein is a process of making a prolongated silica bound zeolite catalyst comprising mixing a zeolite, a prolongated silica, and water to form a mixture, shaping the mixture into a prolongated silica bound zeolite support, and adding one or more catalytic compounds to the prolongated silica bound zeolite support to form the prolongated silica bound zeolite catalyst.

Further disclosed herein is a process for converting hydrocarbons to aromatics comprising: contacting a prolongated silica bound zeolite catalyst comprising at least one Group VIII metal and at least one halide with a hydrocarbon feed in a reaction zone under aromatization conditions; recovering an aromatic product from the reaction zone; and purifying the aromatic product to produce benzene, toluene, paraxylene, orthoxylene, metaxylene, or combinations thereof.

The foregoing has outlined rather broadly the features and technical advantages of the present disclosure in order that the detailed description that follows may be better understood. Additional features and advantages of the embodiments will be described hereinafter that form the subject of the claims of the disclosure. It should be appreciated by those skilled in the art that the conception and the specific embodiments disclosed may be readily utilized as a basis for modifying or designing other structures for carrying out the same purposes of the present disclosure. It should also be realized by those skilled in the art that such equivalent constructions do not depart from the spirit and scope of the embodiments of the disclosure as set forth in the appended claims.

BRIEF DESCRIPTION OF THE DRAWINGS

For a detailed description of the embodiments of the apparatus and methods of the present disclosure, reference will now be made to the accompanying drawing in which:

FIG. 1 is a drawing of a prolate spheroid.

DETAILED DESCRIPTION

Disclosed herein are prolongated silica bound zeolite supports, prolongated silica bound zeolite catalysts, and methods of making and using same. The prolongated silica bound zeolite support may be prepared by blending a zeolite, a prolongated silica, and water to form a mixture and shaping the mixture into the silica bound zeolite support, which is referred to herein as the catalyst base or catalyst support. The prolongated silica bound zeolite catalysts may be prepared by contacting the prolongated silica bound zeolite support with one or more catalytic compounds such as a Group VIII metal (e.g., platinum) and one or more halides (e.g., chloride and fluoride). The prolongated silica bound zeolite catalysts may be used as catalysts in reforming processes such as for example, the conversion of hydrocarbons to aromatics, and may be collectively termed aromatization catalyst compositions. The prolongated silica bound zeolite catalyst compositions disclosed herein may be characterized by an increased concentration of active catalytic material, a reduced temperature start of reaction (TSOR), or both when compared to an otherwise identical composition lacking a prolongated silica.

The prolongated silica bound zeolite support comprises one or more zeolites that are bound together by a binder material. The term "zeolite" generally refers to hydrated, crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms is equal to 2. The framework exhibits a negative electrovalence that typically is balanced by the inclusion of cations within the crystal such as metals, alkali metals, alkaline earth metals, or hydrogen. Thus, zeolites are a group of natural or synthetic hydrated aluminosilicate minerals that contain alkali and alkaline metals. Zeolites are characterized by a framework structure that encloses interconnected cavities occupied by ion-exchangeable large metal cations such as potassium and water molecules permitting reversible dehydration. The actual formula of the zeolite may vary without changing the crystalline structure. In an embodiment, the mole ratio of silicon to aluminum (Si/Al) in the zeolite may vary from about 1.0 to about 3.5.

In an embodiment, the catalyst support comprises a large-pore zeolite. The term "large-pore zeolite" as used herein refers to a zeolite having an effective pore diameter of from about 6 Angstroms (Å) to about 15 Å, alternatively from about 7 Å to about 9 Å. Large pore crystalline zeolites suitable for use in this disclosure include without limitation L-zeolite, X-zeolite, Y-zeolite, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, ZZA-26, SSZ-31, SSZ-33, SSZ-35, SSZ-37, SSZ-41, SSZ-42, SSZ-44, MCM-58, mordenite, faujasite, or combinations thereof. In an embodiment, the large pore zeolite has an isotypic framework structure. In an embodiment, the catalyst support comprises L-zeolite.

L-type zeolites are a sub-group of zeolites. The designations LTL zeolite or Linde type L zeolite also refer to this same sub-group of zeolitic catalysts. Typical L-type zeolites contain mole ratios of oxides in accordance with the following formula:

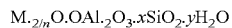

$$M_{2/n}O \cdot OAl_2O_3 \cdot xSiO_2 \cdot yH_2O$$

wherein "M" designates at least one exchangeable cation such as barium, calcium, cerium, lithium, magnesium, potassium, sodium, strontium, and zinc as well as non-metallic cations like hydronium and ammonium ions which may be replaced by other exchangeable cations without causing a substantial alteration of the basic crystal structure of the L-type zeolite. The "n" in the formula represents the valence of "M", "x" is 2 or greater; and "y" is the number of water molecules contained in the channels or interconnected voids with the zeolite. L-zeolite, its X-ray diffraction pattern, its properties, and methods for its preparation are described in detail in U.S. Pat. No. 3,216,789, the content of which is hereby incorporated by reference. In an embodiment, the catalyst support comprises L-zeolite wherein M is potassium, also referred to as KL-zeolite.

The catalyst support further comprises a binder. In an embodiment, the binder comprises a prolongated silica, alternatively a low acidity prolongated silica. FIG. 1 illustrates an embodiment of a prolongated silica, 100. Embodiments of the prolongated silica are characterized generally by a prolated spheroid or ellipsoid shape also termed cigar-shaped, watermelon-shaped, rice-shaped, spindle-shaped or football-shaped. As defined herein a prolate spheroid is a quadric surface in three dimensions obtained by rotating an ellipse about one of its principal axes having a polar diameter longer than its equatorial diameter where a and b are the equatorial radii and c is the polar radius. In a prolate spheroid or ellipsoid a is equal to b but a and b are both less than c. When viewed as a transverse cross section, a is the semi-minor axis, and c is the semi-major axis where c is greater than a in an ellipse. The aspect ratio, as defined herein m is the ratio of c to a.

In an embodiment, the prolongated silica comprises particles having a diameter of from about 5 nm to about 20 nm, alternatively from about 8 nm to about 16 nm and a length of from about 30 nm to about 400 nm, alternatively from about 35 nm to about 350 nm. In an embodiment, the prolongated silica particles may be in the form of a silica sol. A silica sol may be obtained by dispersing the silica particles in water. The silica sol may be provided in about 20 to about 30 vol % aqueous solution having a pH of from about 9.0 to about 10.5 with a viscosity of equal to or less than about 20 mPa·s at 25° C., alternatively from about 1 to about 20 mPa·s at 25° C. An example of a silica sol suitable for use in this disclosure includes without limitation SNOWTEX® UP which is a colloidal silica sol comprising prolongated silica particles that is commercially available from Nissan Chemical Industries Ltd. The binder may additionally comprise synthetic or naturally occurring zeolites; alumina; clays such as montmorillonite and kaolin; the refractory oxides of metals of Groups IVA and IVB of the Periodic Table of the Elements; oxides of silicon, titanium, zirconium or combinations thereof; or combinations thereof.

In an embodiment, the prolongated silica bound zeolite support may be prepared by forming a mixture comprising a zeolite, a prolongated silica, water and optional extrusion aids and then shaped. The mixture may be formed into a suitable shape, for example via extrusion. The mixture may contain from about 85 wt. % to about 95 wt. % zeolite, alternatively from about 75 wt. % to about 90 wt. % zeolite, alternatively from about 50 wt. % to about 95 wt. % zeolite. The mixture may contain zeolite and a prolongated silica binder combined in a weight ratio of from about 1:99 to about 99:1, alternatively from about 90:10 to about 85:15, alternatively from about 92:8 to about 82:18. In an embodiment, the aqueous volume percent of the mixture formed by combining the zeolite and binder (e.g., prolongated silica) may be from about 20% to about 60%, alternatively from about 25% to about 55%, alternatively from about 30% to about 45%. In an embodiment, the mixture will contain sufficient water to retain a desired shape. Water may be added separately to the mixture or as a solution of one or more other components, for example silica sol. The amount of water required to retain a desired shape of the shaped mixture may be varied and selected according to ordinary skill in the art. In an embodiment, the mixture is extruded and may contain up to about 50 grams of water per about 100 grams of extrudate.

In an embodiment, the mixture comprises L-zeolite bound with a prolongated silica, alternatively L-zeolite bound with a prolongated, colloidal silica, alternatively KL-zeolite bound with a prolongated silica, alternatively KL-zeolite bound with a prolongated, colloidal silica.

In an embodiment, the mixture comprising a silica bound zeolite is formed into shaped particles. In an embodiment, the mixture may be formed into any suitable shape. Methods for shaping particles are well known in the art, and include, for example, extrusion, spray drying, pelletizing, agglomerization and the like. In an embodiment, the mixture is formed into an extrudate, for example as described in U.S. Pat. Nos. 5,558,851 and 5,514,362 each of which are incorporated herein in their entirety. In an embodiment, the mixture further comprises an extrusion aid. An extrusion aid may function to improve the rheology of the mixture. This improvement in the rheology of the mixture may function to improve flow of the mixture through the extrusion die. Improved flow through the extrusion die leads to easier equipment start-up, smoother extrusion, faster processing, lower extrusion pressures, and improved product appearance. In an embodiment, the extrusion aid may comprise cellulose derivatives, ethylene glycol, stearic acid or combinations thereof. In an embodiment, the extrusion aid comprises a cellulose ether such as methylcellulose, carboxymethylcellulose, ethylhydroxyethylcellulose, hydroxyethylcellulose, hydroxypropylcellulose, methylhydroxyethylcellulose, methylhydroxypropylcellulose, or combinations thereof. An example of an extrusion aid suitable for use in this disclosure includes without limitation METHOCEL®, a cellulose based material commercially available from Dow Chemical Company. Extrusion aids, their effective amounts and methods of incorporation into mixture may be varied and selected according to ordinary skill in the art. Hereafter the shaped mixture exiting a die will be referred to as the "green extrudate."

Excess water from the green extrudate may be removed by drying to form a dried green extrudate prior to further processing. Conventional methods for drying wet solids can be used to dry the green extrudate, and may include, for example drying in air or an inert gas such as nitrogen or helium. The air or inert gas may be circulating, moving, or static. Drying temperatures may range from about 200° F. to about 400° F., alternatively from about 200° F. to about 300° F., alternatively from about 225° F. to about 275° F. Drying times may range from equal to or greater than about 1 hour, alternatively from about 1 hour to about 10 hours, alternatively from about 2 hours to about 5 hours.

In an embodiment, the dried green extrudate may be calcined to form a calcined extruded base (CEB). Calcination temperatures may range from about 500° F. to about 1500° F., alternatively from about 700° F. to about 1100° F., alternatively from about 850° F. to about 1100° F. Calcination times may range from about 0.5 to about 5 hours, alternatively from about 0.5 to about 1.5 hours. In such embodiments, the calcination may be carried out in an oxygen containing atmosphere having an air flow of from about 10 to about 20 cubic feet per hour (CFH), alternatively the calcination may be carried out in air at a flow of from about 10 to about 20 CFH, alternatively, the calcination may be carried out in "dry" air having an air flow of about 10 to about 20 CFH. As used herein "dry" air refers to air having a dew point of less than about −40° F. The calcined extruded base is a prolongated silica bound zeolite support and may be directly used in a catalyst preparation, see below, or may be further processed according to the following description.

In an embodiment, the CEB may be washed to form a washed CEB. While not wishing to be bound by any one theory, it is believed that washing the CEB may reduce the amount of "readily removable" alkali present. The term washing, as used herein, is meant to include any process where liquid (e.g. water) in excess of the material's pore volume is contacted with the CEB. The "readily removable" alkali is defined herein as the alkali that can be washed out of the CEB after 1, 2, 3, 4, or 5 washings (1:1 volume of liquid to wt of extrudate) at ambient temperature. In an embodiment, the wash water is distilled or deionized water having a pH of from about 5 to about 9. The washing temperature may range from about 70° F. to about 200° F., alternatively of from about 80° F. to about 130° F., alternatively from about 90° F. to about 110° F. The washing time may range from about 5 to about 60 minutes per wash, alternatively from about 15 to about 30 minutes per wash.

After washing to reduce the amount of readily removable alkali, the washed CEB may be dried to form a washed and dried CEB. The drying temperature may range from about 200° F. to about 400° F., alternatively from about 200° F. to about 300° F., alternatively from about 225° F. to about 275° F. The drying time may range from at least about 1 hour, alternatively from about 1 to about 10 hours, alternatively from about 2 to about 5 hours.

The washed and dried CEB may be recalcined to form a washed, dried, and recalcined CEB. The calcining temperature may range from about 500° F. to about 1200° F., alternatively from about 700° F. to about 1100° F., alternatively from about 850° F. to about 1000° F. The calcining time may range from about 0.5 to about 5.0 hours, alternatively from about 0.5 to about 1.5 hours. In such embodiments, the calcination may be carried out in an oxygen containing atmosphere having an air flow of from about 10 to about 20 CFH, alternatively the calcination may be carried out in air at a flow of from about 10 to about 20 CFH, alternatively, the calcination may be carried out in "dry" air having an air flow of about 10 to about 20 CFH. The washed, dried, and recalcined CEB is a prolongated silica bound zeolite support and may be directly used in a catalyst preparation as described herein.

The prolongated silica bound zeolite support having been processed as previously disclosed herein may be further processed to add one or more catalytic compounds to the support. In an embodiment, the addition of a metal and one or more halides to the support forms an aromatization catalyst capable of catalyzing the conversion of hydrocarbons to aromatics.

In an embodiment, the prolongated silica bound zeolite support is impregnated with one or more Group VIII metals to form a metalized prolongated silica bound zeolite support. The metal may be added to the support by employing a variety of known and conventional techniques, e.g., ion-exchange, incipient wetness, pore fill, impregnation, etc. In an embodiment, the metal is added to the support by impregnation with a metal-containing solution. The metal in the metal containing solution may be at least one Group VIII metal; alternatively, Pt, Pd, Rh, Ir, Ru, Os, or combinations thereof; alternatively, platinum. In an embodiment, the metal comprises platinum that is added to the support via contact with a metal-containing solution containing at least one platinum-containing compound. Examples of suitable platinum-containing compounds for contact with the support include without limitation platinum compounds that form positively charged platinum complex ions in solution such as for example platinum salts such as chlorides and nitrates; platinum complexes with amines; or combinations thereof. For example, the platinum-containing compound can be any platinum-containing compound including, but not limited to, ammonium tetrachloroplatinate, chloroplatinic acid, diammineplatinum (II) nitrite, bis-(ethylenediamine)platinum (II) chloride, platinum (II) acetylacetonate, dichlorodiammine platinum, platinum (II) chloride, tetraammineplatinum (II) hydroxide, tetraammineplatinum chloride, tetraammineplatinum (II) nitrate, or combinations thereof. In an embodiment, the platinum source is tetraammine platinum chloride (TAPC). The amount of platinum in the metalized support may range from about 0.1 to about 5 wt. %, alternatively from about 0.1 to about 3 wt. %, alternatively from about 0.3 to about 1.8 wt. %.

In an embodiment, one or more halides are added to the prolongated silica bound zeolite support by contact with a halide-containing compound to form a halided support. The halides may be added to the support separately; alternatively, the halides may be added to the support at the same time. Such halides may be incorporated during the previously described metallization, alternatively the halides may be incorporated during a separate step that may be pre- or post addition of the metal, to form a metalized and halided prolongated silica bound zeolite support. Examples of suitable halides include without limitation fluoride, chloride, bromide, iodide, or combinations thereof. Such halides may be introduced as an organic ammonium halide compound. The organic ammonium halide compound may comprise one or more compounds represented by the formula $N(R)_4X$, where X is a halide and where R represents a hydrogen or a substituted or unsubstituted carbon chain molecule having 1-20 carbons wherein each R may be the same or different. In an embodiment, R is selected from the group consisting of methyl, ethyl, propyl, butyl, and combinations thereof, more specifically methyl. Examples of suitable organic ammonium compounds represented by the formula $N(R)_4X$ include ammonium chloride, ammonium fluoride, and tetraalkylammonium halides such as tetramethylammonium chloride (TMAC), tetramethylammonium fluoride (TMAF), tetraethylammonium chloride, tetraethylammonium fluoride, tetrapropylammonium chloride, tetrapropylammonium fluoride, tetrabutylammonium chloride, tetrabutylammonium fluoride, methyltriethylammonium chloride, methyltriethylammonium fluoride, or combinations thereof. In an embodiment, the halided prolongated silica bound zeolite support comprises chloride present in an amount of from about 0.1 to about 5 wt. %, alternatively from about 0.1 to about 3 wt. %, alternatively from about 0.3 to about 1.8 wt. %. In an embodiment, the halided prolongated silica bound zeolite support comprises fluoride present in an amount of from about 0.1 to about 5 wt.

%, alternatively from about 0.1 to about 3 wt. %, alternatively from about 0.3 to about 1.8 wt. %. In an embodiment, the halided prolongated silica bound zeolite support comprises both chloride and fluoride, which may be present in a Cl:F ratio of from about 1:10 to about 10:1, alternatively from about 1:5 to about 5:1 alternatively from about 1:2 to about 2:1. Once the support has been contacted with halogens and metal it is hereinafter referred to as a halided, metallized support (HMS). In an embodiment, the HMS is allowed to set for several hours prior to additional processing. In an embodiment, the HMS is allowed to set for about 1 to about 24 hours, alternatively for about 2 to about 8 hours, alternatively for about 3 to about 6 hours.

Following the preparation of the HMS by contact with a metal and one or more halides the HMS may then be further processed as described herein. The HMS may be processed to remove undesirable compounds remaining from the contacting steps, for example by drying to remove compounds and/or heating to decompose compounds. In an embodiment, the loaded support is dried, and calcined as described previously.

The HMS may be dried to form a dried HMS, which is an aromatization catalyst. The drying temperature may range from about 100° F. to about 300° F., alternatively from about 150° F. to about 250° F., alternatively from about 200° F. to about 220° F. The drying time may range from about 0.1 to about 6 hours, alternatively from about 0.2 to about 4 hours, alternatively from about 0.2 to about 3 hours. The HMS may be dried using any equipment known to one of ordinary skill in the art for drying under the disclosed conditions. For example, the HMS may be dried using a standard rotary evaporator operating at greater than about 100° F. and under a pressure of about 20 to about 30 inches of mercury.

The dried HMS may be calcined to form a dried and calcined HMS, which is an aromatization catalyst. The calcining temperature may range from about 400° F. to about 900° F., alternatively from about 500° F. to about 700° F., alternatively from about 550° F. to about 600° F. The calcining time may range from about 0.5 to about 5 hours, alternatively from about 0.5 to about 2.5 hours. The calcination may be carried out in an oxygen containing atmosphere under a gas flow rate of from about 5 to about 20 CFH. Alternatively, the calcination may be carried out in air using a flow rate of from about 5 to about 20 CFH, alternatively in dry air using a flow rate of about 5 to about 20 CFH. Upon completion of processing the dried, and calcined HMS may be employed as an aromatization catalyst in a suitable chemical reaction and process.

In an embodiment, the HMS prepared as disclosed herein is used as a catalyst in an aromatization reactor system comprising at least one aromatization reactor and its corresponding processing equipment and will be referred to hereafter as a aromatization catalyst or catalyst. As used herein, the terms "aromatization," "aromatizing" and "reforming" refer to the treatment of a hydrocarbon feed to provide an aromatics enriched product, which in one embodiment is a product whose aromatics content is greater than that of the feed. Typically, one or more components of the feed undergo one or more reforming reactions to produce aromatics. Some of the hydrocarbon reactions that occur during the aromatization operation include the dehydrogenation of cyclohexanes to aromatics, dehydroisomerization of alkylcyclopentanes to aromatics, dehydrocyclization of acyclic hydrocarbons to aromatics, or combinations thereof. A number of other reactions also occur, including the dealkylation of alkylbenzenes, isomerization of paraffins, hydrocracking reactions that produce light gaseous hydrocarbons, e.g., methane, ethane, propane and butane, or combinations thereof.

The aromatization reaction occurs under process conditions that thermodynamically favor the dehydrocyclization reaction and limit undesirable hydrocracking reactions. The pressures may be from about 0 pounds per square inch gauge (psig) to about 500 psig, alternatively from about 25 psig to about 300 psig. The molar ratio of hydrogen to hydrocarbons may be from about 0.1:1 to about 20:1, alternatively from about 0.5:1 to about 6:1. The operating temperatures include reactor inlet temperatures from about 700° F. to about 1050° F., alternatively from about 900° F. to about 1025° F. Finally, the liquid hourly space velocity for the hydrocarbon feed over the aromatization catalyst may be from about 0.1 to about 10, alternatively from about 0.5 to about 2.5.

The composition of the feed is a consideration when designing catalytic aromatization systems. In an embodiment, the hydrocarbon feed comprises non-aromatic hydrocarbons containing at least six carbon atoms. The feed to the aromatization system is a mixture of hydrocarbons comprising $C_6$ to $C_8$ hydrocarbons containing up to about 10 wt % and alternatively up to about 15 wt % of $C_5$ and lighter hydrocarbons ($C_5^-$) and containing up to about 10 wt % of $C_9$ and heavier hydrocarbons ($C_9^+$). Such low levels of $C_9+$ and $C_5^-$ hydrocarbons maximize the yield of high value aromatics. In some embodiments, an optimal hydrocarbon feed maximizes the percentage of $C_6$ hydrocarbons. Such a feed can be achieved by separating a hydrocarbon feedstock such as a full range naphtha into a light hydrocarbon feed fraction and a heavy hydrocarbon feed fraction, and using the light fraction.

In another embodiment, the feed is a naphtha feed. The naphtha feed may be a light hydrocarbon, with a boiling range of about 70° F. to about 450° F. The naphtha feed may contain aliphatic, naphthenic or paraffinic hydrocarbons. These aliphatic and naphthenic hydrocarbons are converted, at least in part, to aromatics in the aromatization reactor system. While catalytic aromatization typically refers to the conversion of naphtha, other feedstocks can be treated as well to provide an aromatics enriched product. Therefore, while the conversion of naphtha is one embodiment, the present disclosure can be useful for activating catalysts for the conversion or aromatization of a variety of feedstocks such as paraffinic hydrocarbons, olefinic hydrocarbons, acetylenic hydrocarbons, cyclic paraffin hydrocarbons, cyclic olefin hydrocarbons, and mixtures thereof, and particularly saturated hydrocarbons.

Preferably, the feedstock is substantially free of sulfur, nitrogen, metals, and other known poisons for aromatization catalysts. In an embodiment, the feedstock contains less than about 100 ppb of sulfur. If present, such poisons can be removed using methods known to those skilled in the art. In some embodiments, the feed can be purified by first using conventional hydrofining techniques, then using sorbents to remove the remaining poisons. Such hydrofining techniques and sorbents are included in the purification process described below.

In an embodiment, the aromatization catalyst may be used for the production of an aromatic product which may then be recovered from the reaction zone and processed subsequently to produce benzene, toluene, paraxylene, orthozylene, metaxylene or combinations thereof. For example, the aromatization catalyst may be used in a process comprising aromatizing a wide boiling range naphtha in a reformer, for example, a continuous catalytic reformer or semi-regenerative reformer, followed by distillation of the reformer effluent into an aromatics fraction. The aromatics fraction may comprise benzene, toluene, paraxylene, orthozylene, metaxylene or combinations thereof.

The xylene isomers orthoxylene, metaxylene, and paraxylene, are important chemical intermediates. Orthoxylene may be oxidized to make phthalic anhydride, which is used to make phthalate-based plasticizers among other things. Metaxylene may be oxidized to make isophthalic acid, which is used in unsaturated polyester resins. Paraxylene may be oxidized to make terephthalic acid, which in turn is used to make polymers such as polytrimethyleneterephthalate, polybutyleneterephthalate (PBT), and polyethyleneterephthalate (PET). PET is one of the largest volume polymers in the world and is used to make PET plastics (e.g., two liter PET bottles). It is also used to make polyester fiber, which in turn is used to make clothes and other fabrics In an embodiment, the aromatization catalyst may be used in the production of benzene which may be hydrogenated to form a hydrogenation product such as for example cyclohexane. For example, the benzene may be hydrogenated in a process involving a high-purity benzene feed and purified hydrogen. The conversion of benzene to cyclohexane is stoichiometric. A large portion of the cyclohexane production is used to produce intermediates for nylons such as for example nylon 6 and nylon 66. Nylon 6 is made by polymerizing caprolactam which is derived from the nitration of cyclohexane. Nylon 66 is made by polymerizing equal molar quantities of adipic acid and hexamethylene diamine (HMDA). Adipic acid is made by a two-step air and nitric acid oxidation of cyclohexane. The adipic acid is converted to HMDA by the reduction of adiponitrile (an intermediate). Adipic acid produced from cyclohexane is also used to manufacture esters for plasticizers and synthetic lubricants, as well as produce polyeurethanes (synthetic leather).

In an embodiment, the aromatization catalyst functions to catalyze the production of benzene which may be further alkylated to produce ethylbenzene which is a raw material for the production of styrene. For example, benzene may be combined, typically in molar excess, with a suitable alkylating reagent having from 2 to 54 carbon atoms such as olefins (e.g., ethylene, propylene), halogenated alkanes, or mixtures thereof. In one embodiment at least a portion of the benzene may be alkylated with ethylene to produce ethylbenzene; which may be optionally followed by dehydrogenation of the ethylbenzene to styrene. In another embodiment at least a portion of the benzene may be alkylated with propylene to produce cumene.

In an embodiment, an prolongated silica bound zeolite catalyst prepared as disclosed herein may have an increased zeolite:binder ratio, e.g., greater than about 80:20 zeolite:binder, when compared to an otherwise identical silica bound zeolite catalyst lacking a prolongated silica as a binder. By having more zeolite and less binder, a catalyst support may be prepared having an increased surface area for impregnation (e.g., Pt loading) and/or dispersion (e.g., Pt dispersion), thereby providing for a catalyst having higher levels of catalytically active materials than an otherwise identical catalyst lacking a prolongated silica as a binder. Alternatively, an catalyst prepared as disclosed herein and having a traditional zeolite:binder ratio, e.g., equal to or less than about 80:20 zeolite:binder, may provide an catalyst with sufficient particle strength suitable for use in a fluidized or moving catalyst bed. For example, an catalyst comprising about 80:20 zeolite:prolongated silica may be sufficiently robust to withstand a continuous catalyst regeneration process, in contrast to an otherwise identical catalyst lacking a prolongated silica as a binder that is traditionally employed in a fixed catalyst bed to avoid damage to the catalyst.

The resulting prolongated silica bound zeolite catalyst may display improvements in catalytic performance consistent with the higher levels of catalytically active materials. Improvements in catalytic performance may be measured by any means known to one of ordinary skill in the art. When used as catalysts in an aromatization reaction, the catalyst of this disclosure may display a reduced Temperature at Start of Run (TSOR), a decreased fouling rate, higher liquid yield, an extended catalytic life, or combinations thereof. The prolongated silica bound zeolite catalysts may have a TSOR of from about 900° F. to about 937° F., alternatively of from about 907° F. to about 930° F., alternatively of from about 910° F. to about 924° F. The prolongated silica bound zeolite catalysts of this disclosure may be further characterized by a lifetime that is equal to or about 10% greater than an otherwise identical catalyst lacking a prolongated silica, alternatively equal to or about 20% greater, alternatively about 30% greater. Additional measures of improved catalytic performance would be apparent to one of ordinary skill in the art.

EXAMPLES

The invention having been generally described, the following examples are given as particular embodiments of the invention and to demonstrate the practice and advantages thereof. It is understood that the examples are given by way of illustration and are not intended to limit the specification of the claims to follow in any manner.

Example 1

Preparation of Prolongated Silica Bound KL-Zeolite

Support A was a prolongated silica bound KL-Zeolite containing about 88 wt % KL-Zeolite. A mixture was prepared from about 671.9 grams (g) of L zeolite and about 30 g of methyl cellulose. This mixture was thoroughly blended in a muller before proceeding to the next step. To this mixture, about 400 g of an about 20 wt % aqueous solution of the prolongated silica (SNOWTEX®-UP, Nissan Chemical Industries) was added and thoroughly blended. To accomplish thorough blending the silica sol was added to the muller over an about 11 minute period. After the silica sol was added to the mixture, water was added to bring the moisture to a level of about 35 wt % to about 40 wt % loss on ignition (LOI) for extrusion. Loss on ignition is the percentage of weight lost when a sample is heated at about 1000° F. for about 1 hour in dry air. The mixture was then extruded through a 1/16 inch (1.6 mm) die. The extrudates were then dried at about 250° F. (121° C.) for about 4 hours, followed by calcination for about 1 hour at about 932° F. (500° C.). An about 100 g portion of the calcined extrudate was then washed with about 250 mL of about 100° F. (37.8° C.) deionized water. This wash time was sufficient to achieve good contacting of the solids and liquids. This washing was repeated for a total of three washings. The washed extrudate was then dried for about 4 hours at about 250° F. (121° C.) and then calcined in air at about 900° F. (482° C.) for about 1 hour in flowing dry air.

Support B was a prolongated silica bound KL-Zeolite containing about 80 wt % KL-Zeolite. This support was prepared according to the same method as Support A with the exception that a about 30 wt % aqueous solution of the prolongated silica was used.

Support C was a spherical silica bound KL-Zeolite containing about 80 wt % KL-Zeolite. This support was prepared according to U.S. Pat. No. 6,207,042 using Tosoh L-Zeolite, SI-350 Silica Sol, obtained from CCIC (Japan), and Methocel®, obtained from Dow Chemical Company, as an extrusion aid.

Example 2

Impregnation of Prepared Supports

Catalyst D comprised about 1 wt % Pt on prolongated silica bound KL-Zeolite containing about 88 wt % KL-Zeolite. The platinum-impregnated KL-zeolite catalyst containing about 1.0 wt % platinum was prepared in the following manner. An impregnating mixture of about 1.52 g tetraammineplatinum (II) chloride (TAPC), about 1.41 g ammonium fluoride (AF), about 0.64 g ammonium chloride (AC) and about 40.89 g water was formed and added to a container containing about 80.17 g of the prolongated silica bound KL-zeolite extrudates of Support A using incipient wetness techniques. The impregnated extrudates were then allowed to stand for about 4 hours at room temperature. The impregnated KL-zeolite was dried in a vacuum for about 3 hours at about 212° F. and then calcined at about 585° F. for 1 hour in flowing dry air. The resultant extrudates contained about 0.94 wt % Pt, about 0.95 wt % F, and about 0.67 wt % Cl as determined by standard analytical techniques.

Catalyst E comprised about 0.5 wt % Pt on prolongated silica bound KL-Zeolite containing about 88 wt % KL-Zeolite. The platinum-impregnated KL-zeolite catalyst containing about 0.5 wt % platinum was prepared according to the method described for Catalyst D with the following exceptions. The impregnating mixture instead contained about 0.75 g tetraammineplatinum (II) chloride (TAPC), about 1.45 g ammonium fluoride (AF), about 0.88 g ammonium chloride (AC) and about 40.89 g water. The extrudate was formed and added to a container containing about 80.17 g of the prolongated silica bound KL-zeolite extrudates of Support A. The resultant extrudates contained about 0.49 wt % Pt, 0.65 wt % F, and about 0.48 wt % Cl by standard analytical techniques.

Catalyst F comprised about 1.0 wt % Pt on prolongated silica bound KL-Zeolite containing about 80 wt % KL-Zeolite. The platinum-impregnated KL-zeolite catalyst containing about 1.0 wt % platinum was prepared in the following manner. An impregnating mixture of about 1.52 g tetraammineplatinum (II) chloride monohydrate (TAPC), about 1.41 g ammonium fluoride (AF), about 0.64 g ammonium chloride (AC) and about 41.84 g water was formed and added to a container containing about 80.46 g of the prolongated silica bound KL-zeolite extrudates of Support B using incipient wetness techniques. The impregnated extrudates were then allowed to stand for about 4 hours at room temperature. The impregnated KL-zeolite was dried in a vacuum for about 3 hours at about 212° F. (100° C.) and then calcined at about 585° F. (307° C.) for about 1 hour in flowing dry air. The resultant extrudates contained about 0.97 wt % Pt, about 0.61 wt % F, and about 0.63 wt % Cl by standard analytical techniques.

Catalyst G about comprised about 1 wt % Pt on a spherical-silica bound KL-Zeolite containing about 80 wt % KL-Zeolite. A platinum-impregnated KL-zeolite catalyst containing about 1.0 wt % platinum was prepared according to U.S. Pat. No. 6,207,042. The resultant extrudates contained about 0.98 wt % Pt, about 0.68 wt % F, and about 0.82 wt % Cl by standard analytical techniques.

Example 3

Catalyst Evaluations

Each of the extrudates from Example 2 were then ground and sieved to about 20-40 mesh (0.84 mm-0.42 mm diameter) and placed in a reactor comprising an about ¼ inch OD (6.4 mm) stainless steel reactor vessel in a temperature controlled furnace. The catalyst was dried and reduced under flowing hydrogen without recycle at a temperature from room temperature to about 950° F. (510° C.). The reactor was then cooled to about 930° F. (499° C.), and a feed stream of aliphatic hydrocarbons at a liquid hourly space velocity (LHSV) of about 12 $hr^{-1}$ and hydrogen at $H_2$:hydrocarbon mole ratio of about 1 was introduced to the reactor vessel at a feed rate of about 12 mL/min and a pressure of about 100 psig. The reactor effluent composition was regularly analyzed by gas chromatography to indicate the weight percentage of total aromatics in the $C_{5+}$ fraction. The reactor temperature was then adjusted to achieve the desired total wt % aromatics in the $C_{5+}$ product, typically about 70 wt %, and performance data was then collected.

The catalysts prepared in accordance with Examples 1 and 2 below illustrate effects of the prolongated silica morphology on the catalyst efficiency. The results are summarized in Table 1.

TABLE 1

| Impregnated Support | Silica Morph. | Zeolite:Binder (Wt Ratio) | Pt (Wt %) | TSOR | Fouling Rate ° F./hr (° C./hr) | $C_{5+}$ (Wt %) |
|---|---|---|---|---|---|---|
| D | Prolongated | 88:12 | 1 | 907° F. (486° C.) | 0.14 (0.078) | 92.4 |
| E | Prolongated | 88:12 | 0.5 | 937° F. (503° C.) | 0.25 (0.14) | 92.4 |
| F | Prolongated | 80:20 | 1 | 924° F. (501° C.) | 0.18 (0.10) | 93.1 |
| G (comparison) | Spherical | 80:20 | 1 | 931° F. (499° C.) | 0.20 (0.11) | 91.9 |

The results in Table 1 demonstrate that the substitution of spherical silica with prolongated silica increased the zeolite:binder ratio resulting in a reduction in TSOR while producing comparable levels of aromatics.

While various embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention described in the specification above. The discussion of a reference in the disclosure is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A process for converting hydrocarbons to aromatics comprising:
    contacting a catalyst composition comprising a prolongated silica bound zeolite, at least one Group VIII metal, and at least one halide with a hydrocarbon feed in a reaction zone under aromatization conditions wherein the prolongated silica bound zeolite comprises a KL zeolite, and wherein the hydrocarbon feed comprises naptha;
    recovering an aromatic product from the reaction zone; and
    purifying the aromatic product to produce benzene, toluene, paraxylene, orthoxylene, metaxylene, or combinations thereof.

2. The process of claim 1 wherein the hydrocarbon feed contains less than about 100 ppb of sulfur.

3. The process of claim 1 further comprising hydrogenating all or a portion of the benzene to produce cyclohexane.

4. The process of claim 1 further comprising alkylating all or a portion of the benzene with ethylene to produce ethylbenzene, and optionally dehydrogenating the ethylbenzene to produce styrene.

5. The process of claim 1 further comprising alkylating all or a portion of the benzene with propylene to produce cumene.

6. The process of claim 1 wherein the Group VIII metal comprises a platinum compound.

7. The process of claim 6 wherein the platinum compound comprises ammonium tetrachloroplatinate, chloroplatinic acid, diammineplatinum (II) nitrite, bis-(ethylenediamine) platinum (II) chloride, platinum (II) acetylacetonate, dichlorodiammine platinum, platinum (II) chloride, tetraammineplatinum (II) hydroxide, tetraammineplatinum chloride, tetraammineplatinum (II) nitrate, or combinations thereof.

8. The process of claim 6 wherein the platinum compound is present in an amount of from about 0.1 wt. % to about 5 wt. %.

9. The process of claim 1 wherein the catalyst composition has a reduced temperature at start of run when compared to an otherwise identical catalyst composition lacking a prolongated silica bound zeolite.

10. The process of claim 1 wherein the catalyst composition has a decreased fouling rate when compared to an otherwise identical catalyst composition lacking a prolongated silica bound zeolite.

11. The process of claim 1 wherein the catalyst composition has an increased liquid yield when compared to an otherwise identical catalyst composition lacking a prolongated silica bound zeolite.

12. The process of claim 1 wherein the catalyst composition has a catalytic lifetime that is at least about 10% greater than the catalytic lifetime of an otherwise identical catalyst composition lacking a prolongated silica bound zeolite.

13. The process of claim 1 wherein the at least one halide comprises a fluoride compound, a chloride compound, or combinations thereof.

14. The process of claim 1 wherein the ratio of prolongated silica binder to prolongated silica bound zeolite is greater than about 80:20.

15. The process of claim 1 wherein the prolongated silica has a diameter of from about 5 nm to about 20 nm and a length of from about 30 nm to about 400 nm.

16. The process of claim 1 wherein the catalyst composition and the hydrocarbon feed are contacted in an environment having a pressure from about 25 pounds per square inch gauge (PSIG) to about 300 PSIG.

17. The process of claim 1 wherein the catalyst composition and the hydrocarbon feed are contacted in the reaction zone at a temperature of from about 700° F. to about 1050° F.

18. The process of claim 1 wherein the catalyst composition and the hydrocarbon feed are contacted such that the space velocity for the hydrocarbon feed over the catalyst composition is from about 0.5 to about 2.5.

19. The process of claim 1 wherein the hydrocarbon feed comprises hydrogen and hydrocarbons in a ratio of from about 0.5:1 to about 6:1.

20. The process of claim 1 wherein the aromatic product is a product of dehydrogenating cyclohexanes to yield an aromatic, dehydroisomerizating alkylcyclopentanes to yield an aromatic, dehydrocyclizating acyclic hydrocarbons to yield an aromatic, or combinations thereof.

21. The method of claim 1 further comprising purifying the feedstock prior to contacting with the catalyst composition.

22. The process of claim 1 further comprising oxidizing orthozylene, metazylene, or parazylene.

23. A process for converting hydrocarbons to aromatics comprising:
    contacting a catalyst composition comprising a prolongated silica bound zeolite, at least one Group VIII metal, and at least one halide with a hydrocarbon feed in a reaction zone under aromatization conditions wherein the prolongated silica bound zeolite comprises a KL zeolite, wherein removable alkalis have been removed from the prolongated silica bound zeolite, and wherein the hydrocarbon feed comprises naptha;
    recovering an aromatic product from the reaction zone; and
    purifying the aromatic product to produce benzene, toluene, paraxylene, orthoxylene, metaxylene, or combinations thereof.

* * * * *